(12) United States Patent
Sabourin et al.

(10) Patent No.: US 7,415,371 B2
(45) Date of Patent: Aug. 19, 2008

(54) SYSTEMS AND METHODS FOR PROACTIVE DETECTION OF IMAGING CHAIN PROBLEMS DURING NORMAL SYSTEM OPERATION

(75) Inventors: Thomas James Sabourin, Milwaukee, WI (US); Gregory Charles Stratton, Wauwatosa, WI (US); Michael Richard Mortiz, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 139 days.

(21) Appl. No.: 11/490,289

(22) Filed: Jul. 20, 2006

(65) Prior Publication Data

US 2008/0021316 A1   Jan. 24, 2008

(51) Int. Cl.
*G06F 19/00* (2006.01)

(52) U.S. Cl. ......................................... 702/69; 356/73
(58) Field of Classification Search ......... 702/182–185, 702/188; 356/73, 300
See application file for complete search history.

(56) References Cited

U.S. PATENT DOCUMENTS 6,381,557 B1 *   4/2002   Babula et al. ............... 702/183

* cited by examiner

*Primary Examiner*—Edward Raymond
(74) *Attorney, Agent, or Firm*—McAndrews, Held & Malloy, Ltd.; Peter J. Vogel; Michael A. Dellapenna

(57) ABSTRACT

Certain embodiments of the present invention provide a method for performing diagnostics in a medical imaging system during the normal operating mode of the imaging system including firing a diagnostic vector with a probe, collecting signal data based at least in part on the diagnostic vector, and processing the signal data to determine a diagnostic status. The diagnostic status indicates an operating condition of at least one component of the medical imaging system.

18 Claims, 4 Drawing Sheets

SYSTEMS AND METHODS FOR PROACTIVE DETECTION OF IMAGING CHAIN PROBLEMS DURING NORMAL SYSTEM OPERATION

BACKGROUND OF THE INVENTION

The present invention generally relates to medical imaging. In particular, the present invention relates to systems and methods for proactive detection of imaging chain problems during normal system operation.

Imaging systems encompass a variety of imaging modalities, such as x-ray systems, computerized tomography (CT) systems, ultrasound (US) systems, electron beam tomography (EBT) systems, magnetic resonance (MR) systems, and the like. Imaging systems generate images of an object, such as a patient. The images may be generated, for example, through exposure to an energy source or wave. For example, ultrasound beams may travel into a patient and produce echo signals reflected from bone and tissue inside the patient. As another example, an x-ray source may be used to generate x-rays that pass through an object. The x-rays may be partially absorbed by the object and an image may be generated based on the energy that passes through the object.

The generated images may be used for many purposes. For instance, internal defects in an object may be detected. Additionally, changes in internal structure or alignment may be determined. Fluid flow within an object may also be represented. Furthermore, the images may show the presence or absence of structures in an object.

The images generated by medical imaging systems may be used to assist a physician in making an accurate diagnosis. For example, a physician may use one or more images to visually identify a lesion or other anomalous structure in a patient. As another example, a physician may compare images taken over a series of patient visits to examine the evolution of a structure and/or to evaluate the effectiveness of a treatment. That is, the physician may examine morphological changes, such as changes in size and/or shape, of a lesion to evaluate its characteristics and/or the effectiveness of therapy.

In an ultrasound imaging system, for example, a sequence of beams or sound waves is generated by a probe. The transmitted waves are reflected or scattered from the object being scanned. Some of the waves may only be partially reflected. The reflected signals are received by the probe. The received signals are then read out from the probe and processed to create a digital image.

The ultrasound beams generated by an ultrasound imaging system are based on a scan sequence. The scan sequence includes a series of vectors that specify the parameters of the beam to be generated by the probe. The parameters may include amplitude and direction, for example. The vectors may be based on the kind of image desired and/or an scanning mode. For example, in a B-mode image, the scan sequence may specify a series of vectors to fan the beam through a plane to generate a two-dimensional image. As another example, a pulsed wave mode may be used for examining blood flow. A scan sequence may include and/or mix different kinds of vectors. For example, a scan sequence may include 100 B-mode beams mixed with 86 color beams.

Another type of vector that may be included in a scan sequence is a "junk" or "conditioning" vector. A junk vector may be used to set up initial conditions for subsequent vectors and/or when switching modes. A junk vector may be fired when it is desirable for a subsequent vector to have acoustic energy in tissue, for example. For example, in a sequence of color firings 0 through 10, a junk vector may be added to the sequence at firing −1, yielding the same side-effects regarding acoustic energy in the tissue for the actual color firings.

The reflected signals from the beams are received by the ultrasound probe. The reflected signals are then processed by the imaging chain of the ultrasound system. That is, the signals are read out of the transducer of the probe and then processed to generate one or more images.

Current medical imaging systems, such as ultrasound systems, may include system diagnostics that reside on the system for assessing problems with imaging performance. Such diagnostic systems are passive. That is, a field service person and/or operator must manually invoke the diagnostics. For example, a field service engineer may manually invoke one or more diagnostic checks either in person or remotely. Running these diagnostics results in downtime for the users of the system. In other words, while the diagnostic system is being utilized, the imaging system cannot be used for its normal operations. Thus, it is highly desirable to have an active system-health monitoring capability that runs when the system is being used for normal operations.

Certain aspects of an imaging system may be easily monitored. For example, power supply voltages, system temperatures, or the data error rates of a network connection may be relatively simple to check the status of. However, current systems are unable to actively monitor the status of the image chain. That is, failures, errors, and/or artifacts in the imaging chain that may be indicative of larger or developing system failures are not easily monitored in current systems. Thus, it is highly desirable to be able to actively monitor the status of the image chain.

Therefore, there is a need for an active system-health monitoring capability that runs when the system is being used for normal operations. In addition, there is a need for the ability to actively monitor the status of the image chain. Thus, there is a need for systems and methods for proactive detection of imaging chain problems during normal system operation.

BRIEF SUMMARY OF THE INVENTION

Certain embodiments of the present invention provide a method for performing diagnostics in a medical imaging system during the normal operating mode of the imaging system including firing a diagnostic vector with a probe, collecting signal data based at least in part on the diagnostic vector, and processing the signal data to determine a diagnostic status. The diagnostic status indicates an operating condition of at least one component of the medical imaging system.

Certain embodiments of the present invention provide a system for evaluating the status of a medical imaging system including an acquisition component and a processing component. The acquisition component is adapted to fire a diagnostic vector during normal system operation. The acquisition component is adapted to collect a signal based at least in part on the diagnostic vector. The processing component is adapted to determine a diagnostic status of a component of the medical imaging system based at least in part on the signal.

Certain embodiments of the present invention provide a computer-readable medium including a set of instructions for execution on a computer, the set of instructions including a firing routine, an acquisition routine, and a processing routine. The firing routine is configured to fire a diagnostic vector. The acquisition routine is configured to collect a signal based at least in part on the diagnostic vector. The processing routine is configured to determine a diagnostic status of a component of a medical imaging system based at least in part on the signal.

Figure 1:
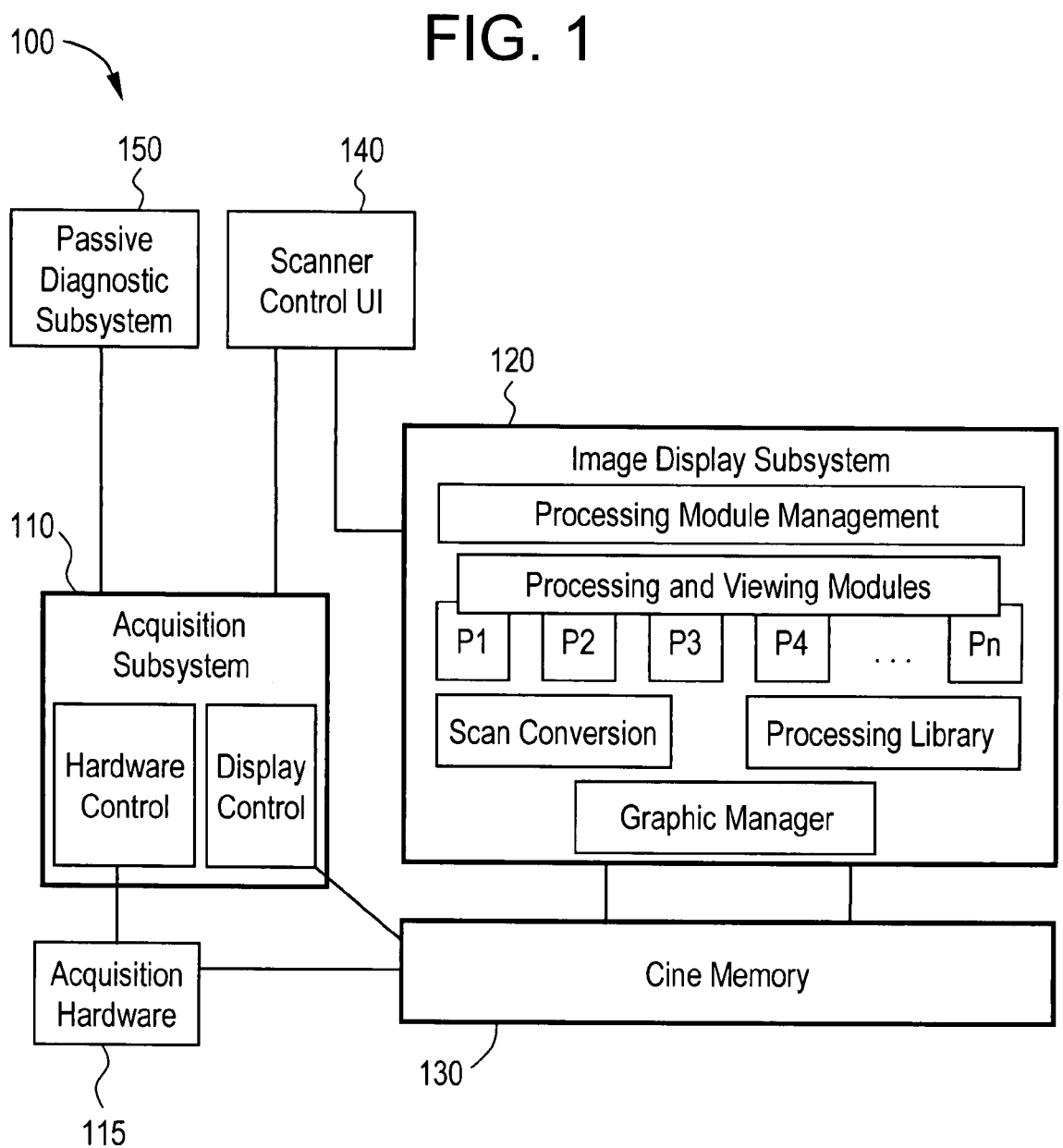
FIG. 1 illustrates a medical imaging system according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 illustrates a medical imaging system 100 according to an embodiment of the present invention. The medical imaging system 100 includes an acquisition subsystem 110, acquisition hardware 115, an image display subsystem 120, a memory component 130, an interface component 140, and a passive diagnostic subsystem 150. The acquisition subsystem 110 is in communication with the acquisition hardware 115 and the memory component 130. The acquisition hardware 115 is in communication with the acquisition subsystem 110 and the memory component 130. The image display subsystem 120 is in communication with the memory component 130 and the interface component 140. The interface component 140 is in communication with the acquisition subsystem 110 and the image display subsystem 120. The passive diagnostic subsystem 150 is in communication with the acquisition subsystem 110.

The acquisition subsystem 110 may include hardware control and/or display control components. The hardware control component controls the acquisition hardware 115. For example, the hardware control component may configure and initiate the acquisition of an image using the acquisition hardware 115. The display control component provides information corresponding to the data acquired by the acquisition hardware 115. The display control component may store the information in the memory component 130, for example.

The acquisition hardware 115 is adapted to acquire signal data for the generation of medical images. The acquisition hardware 115 may include, for example, a probe, such as an ultrasound transducer and readout electronics. The acquisition hardware 115 may emit energy, such as ultrasound waves and may receive signal data based at least in part on the emitted energy. The acquisition hardware 115 provides acquired signal data to the memory component 130.

The image display subsystem 120 may include one or more processing modules. The processing modules are used to process and/or display data in the memory component 130. In addition, the image display subsystem 120 may include additional utilities, libraries, and/or modules to aid or support the processing and/or display of data such as the data in the memory component 130.

The memory component 130 is adapted to store, hold, and/or provide data acquired from the acquisition hardware 115. For example, the memory component 130 may store signal data acquired from the acquisition hardware 115. As another example, the memory component 130 may provide the stored signal data to the image display subsystem 120 for processing and/or display. The memory component 130 may be adapted to store signal data grouped as frames and/or volumes, for example. A frame of signal data may be a two-dimensional plane or a three-dimensional volume, for example. In addition, the memory component 130 may be adapted to keep associated information, such as tags relating to the type, nature, and/or contents of stored data. The associated information may be provided by the acquisition subsystem 110, for example. The associated information may include configuration parameters of the acquisition hardware 115 such as imaging depth. The memory component 130 may be a cine memory, for example.

The interface component 140 is adapted to control the acquisition subsystem 110 and/or the image display subsystem 120. For example, the interface component 140 may control the acquisition subsystem 110 to initiate the acquisition of signal data and may in turn control the image display subsystem 120 to process the acquired data to create a medical image and then display the medical image. The interface component 140 may be used by a user. For example, a physician may use the interface component 140 to configure the imaging system 100 to acquire data, process the data, and display the processed data as a medical image.

The passive diagnostic subsystem 150 is adapted to initiate and/or perform one or more diagnostic tests on one or more components of the medical imaging system 100. The passive diagnostic subsystem 150 initiates and/or performs the test at the command of a user, such as a field service representative or operator. A user manually causes the passive diagnostic subsystem 150 to initiate and/or perform one or more diagnostic tests. A passive diagnostic test may be initiated locally or remotely. That is, a user cause the passive diagnostic subsystem 150 to initiate the test when the user is physically proximate to the medical imaging system 100 or remotely over a network, for example. During the operation of the passive diagnostic subsystem 150, the medical imaging system 100 may not be used for normal operations, such as acquiring, processing, and/or displaying signals and/or images. In certain embodiments, the medical imaging system 100 does not include a passive diagnostic subsystem 150.

In operation, a user typically configures and/or initiates the acquisition of medical images with the medical imaging system 100 using the interface component 140. For example, the user may specify a sequence of images to be acquired or one or more imaging modes to be used. For example, in an ultrasound system, the user may configure the imaging system to acquire a series of B-mode images.

The interface component 140 sends commands and/or data based on the user's input to the acquisition subsystem 110 and/or the image display subsystem 120. For example, the interface component 140 may indicate to the acquisition subsystem that a pulsed wave mode be used. The acquisition subsystem 110 may, in turn, generate a scan sequence based on the commands and/or data from the interface component 140. The scan sequence may, as discussed above, include one or more vectors configured to generate ultrasound beams to acquire the desired signal data.

The acquisition subsystem 110 controls the acquisition hardware 115 to generate an ultrasound beam based on the vector(s) in the scan sequence. For example, the acquisition hardware 115 may beam-form based on the vector(s) from the acquisition subsystem 110 to acquire data. The acquisition hardware 115 may fire or emit a beam using an ultrasound transducer, for example.

In certain embodiments, the reflected and/or scattered energy from the emitted energy is sensed at least in part by the acquisition hardware 115. For example, reflected ultrasound energy may be sensed by one or more channels in an ultrasound transducer in the acquisition hardware 115. The received signals are read from the transducer and stored in the memory component 130. The received signals from one or more vectors may be combined to generate an image frame.

In addition to vectors configured to acquire B-mode or pulsed wave data, embodiments of the present invention support diagnostic vectors. A diagnostic vector may be adapted to acquire data relating to one or more components of the medical imaging system 100. That is, unlike a B-mode vector which is configured to support the generation of a two-dimensional medical image, a diagnostic vector is specified with parameters to allow the acquisition of diagnostic data that may be used to determine a diagnostic status of one or more components of the medical imaging system 100. The diagnostic status may indicate the operating condition of the components, for example. The design and setup of each diagnostic vector may be customized for the part of the system to be tested. For example, a diagnostic vector may be configured to aid in determining a diagnostic status for one or more components of the imaging chain of the medical imaging system 100 to indicate proper or improper functioning of the component(s).

In certain embodiments, one or more diagnostic vectors may be inserted into the scan sequence at a number of times. In certain embodiments, one or more diagnostic vectors are inserted into the scan sequence during normal operation of the medical imaging system 100. Multiple diagnostic vectors may be inserted into the scan sequence consecutively, for example. Alternatively, multiple diagnostic vectors may be inserted in the scan sequence separated by one or more non-diagnostic vectors, such as B-mode or color Doppler vectors.

In certain embodiments, diagnostic vectors may be inserted into the scan sequence once per frame. In certain embodiments, a diagnostic vector is inserted into the scan sequence when the medical imaging system 100 is idle. In certain embodiments, a diagnostic vector is inserted into the scan sequence in place of a conditioning or junk vector. For example, rather than inserting a conditioning vector for which signal data may be ignored, a diagnostic vector may be inserted which can serve a similar purpose as the conditioning vector and may be used to acquire diagnostic status information relating to one or more components of the medical imaging system 100.

In certain embodiments, a diagnostic vector may be fired when the probe is in the air. In the case of an ultrasound probe, when the probe is not in contact with the object being imaged, the medical imaging system 100 may be capable of determining that the probe is in the air and may take the opportunity to insert one or more diagnostic vectors into the scan sequence, for example. For example, the received signal from the one or more diagnostic vectors at very shallow depths where the acoustic ring-down of the transducer is present may be examined. Alternatively, the noise present in the received signal at deeper depths where no ring-down is present, and thus, little signal and no patterns should be received, may be examined. In either or both cases, the status of one or more elements of the acquisition hardware 115 and/or the read channels of the medical imaging system 100 may be tested.

The medical imaging system 100 may support a freeze mode. Freeze mode is when a user wishes to stop the live acquisition of data to look at the currently displayed image for printing or storing or to review previous images from the memory component 130, which may also be printed or stored, for example. In certain embodiments, one or more diagnostic vectors may be inserted into the scan sequence when the medical imaging system 100 is about to enter a freeze mode. That is, just prior to entering the freeze mode, one or more diagnostic vectors may be fired. For example, a user may indicate via the interface component 140 that the medical imaging system 100 is to be placed into a freeze mode. Before engaging the freeze mode, the medical imaging system 100 may insert one or more diagnostic vectors into the scan sequence to take the opportunity to perform one or more diagnostic tests when they will not interfere with normal imaging operations.

Similarly, in certain embodiments, one or more diagnostic vectors may be inserted into the scan sequence when the medical imaging system 100 is about to come out of freeze to resume scanning. That is, just prior to leaving the freeze mode, one or more diagnostic vectors may be fired. For example, a user may indicate via the interface component 140 that the medical imaging system 100 is to be taken out of freeze mode. Before resuming scanning, the medical imaging system 100 may insert one or more diagnostic vectors into the scan sequence to take the opportunity to perform one or more diagnostic tests when the diagnostic vectors and/or the diagnostic tests will not interfere with normal imaging operations.

The memory component 130 is adapted to store signal data. The signal data may include acquired signal data from the acquisition subsystem 110 and/or the acquisition hardware 115, for example. The memory component 130 may store the signal data individually and/or as part of one or more frames and/or volumes. For example, a scan sequence may be used to generate 128 ultrasound beams, the signal data from which may be stored as a single frame. Information about the scan sequence, scanning mode, and/or vector used to acquire the signal data and/or the frame may also be stored in the memory component 130. For example, the data in the memory component 130 may be associated with tags indicating the type of the data and/or parameters relating to the data.

In addition to storing signal data received from the acquisition subsystem 110 and/or the acquisition hardware 115, the memory component 130 may be adapted to store data that has been processed by the image display subsystem 120. For example, the image display subsystem 120 may process one or more frames of data stored in the memory component 130 and store the processed frames in the memory component 130 so that the frames may be displayed by the image display subsystem 120.

The image display subsystem 120 is adapted to process data. The data may be data stored in the memory component 130, for example. The data may be signal data from the acquisition subsystem 110 and/or the acquisition hardware 115, for example. For example, the image display subsystem 120 may process a frame of data acquired by the acquisition hardware 115 and stored in the memory component 130. Processing the data may include, for example, perform signal processing, image processing, and/or display processing on the data. For example, the image display subsystem 120 may utilize signal processing routines on a frame of data to generate an image, and then use image processing routines on the image to enhance it. Finally, the image display subsystem 120 may process the enhanced image by displaying it on a monitor to a user. The image display subsystem 120 may display the data, the processed data, and/or one or more images based at least in part on the data using the interface component 140.

The image display subsystem 120 may include libraries, converters, management components, and/or processing modules to aid in processing the data. The data may be processed by one or more processing modules, for example. The processing modules may be chained to perform different kinds of processing on data. As discussed above, the data to be processed by the image display subsystem 120 may be stored in the memory component 130. When one processing module has performed its processing on data, it may store the processed data in the memory component 130. Then a second processing module may retrieve the processed data from the memory component 130 and process it further. Thus, the processing module may be chained by storing processed intermediate data in the memory component 130. Alternatively, data may be passed directly from one processing module to another to chain the processing module.

In addition to the data processing described above, in certain embodiments, the image display subsystem 120 is adapted to process diagnostic signal data. The diagnostic signal data may be acquired by the acquisition hardware 115 based at least in part on one or more diagnostic vectors, for example. The diagnostic signal data may, similar to the signal data and processed data and images discussed above, be stored in the memory component 130. In certain embodiments, the image display subsystem 120 includes one or more processing modules, similar to the processing modules discussed above, for processing the diagnostic signal data. The diagnostic signal data may be processed to determine a diagnostic status of one or more components of the medical imaging system 100, for example. The diagnostic status may then be displayed to a user, reported to a field service engineer, provided to a system health monitoring component for analysis, and/or stored in a log file, for example. The diagnostic status may indicate the operating condition of the components, for example. For example, the diagnostic status may indicate the operating condition of a read element of the acquisition hardware 115. As another example, the diagnostic status may indicate the operating condition of a read channel of the medical imaging system 100.

In one embodiment, for example, the medical imaging system 100 is adapted to perform a channel-alive test. The channel-alive test may be performed during normal system operation, for example. Suppose the acquisition hardware 115 includes 128 channels. The acquisition subsystem 110 may insert 128 diagnostic vectors into a scan sequence. The diagnostic vectors may be inserted consecutively. Alternatively, the diagnostic vectors may be mixed with other vectors, as discussed above. In this case, each diagnostic vector may be configured to be equivalent to the center vector. That is, the vector may be centered in the aperture and directed perpendicular to the transducer surface. Whereas a normal B-mode scan sequence may make use of a similarly configured vector, when a diagnostic vector in the scan sequence is fired, the acquisition hardware 115 may be configured to enable only a single read channel. For example, the acquisition subsystem 110 may pass the diagnostic vector to the acquisition hardware 115 and indicate that when the acquisition hardware 115 receives signal data based on the fired diagnostic vector, only one read channel be enabled. For each of the 128 diagnostic vectors, each of the 128 channels may be enabled—one per vector. Thus, by turning on a different channel for each of the diagnostic vectors, the signal data from each channel may be individually analyzed, unlike in a typical B-mode scan, where signal data would be acquired from most or all of the read channels. The signal data may be stored in the memory component 130, for example. The signal data may be analyzed by the image display subsystem 120, for example.

In one embodiment, for example, the medical imaging system 100 is adapted to utilize a sequence of diagnostic vectors which are configured with different spectral properties. For example, each diagnostic vector may use a different narrowband transmit pulse. The frequencies of the pulses may be selected to span the bandwidth of the acquisition hardware 115. The received signals from each pulse may then be received and processed to evaluate a bandpass filtering capability of the signal chain of the medical imaging system 100. As another example, the received signals from each pulse may be received and processed to test the performance of a fixed demodulation applied to the signals.

As discussed above, the components, elements, and/or functionality of the medical imaging system 100 may be implemented alone or in combination in various forms in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Figure 2:
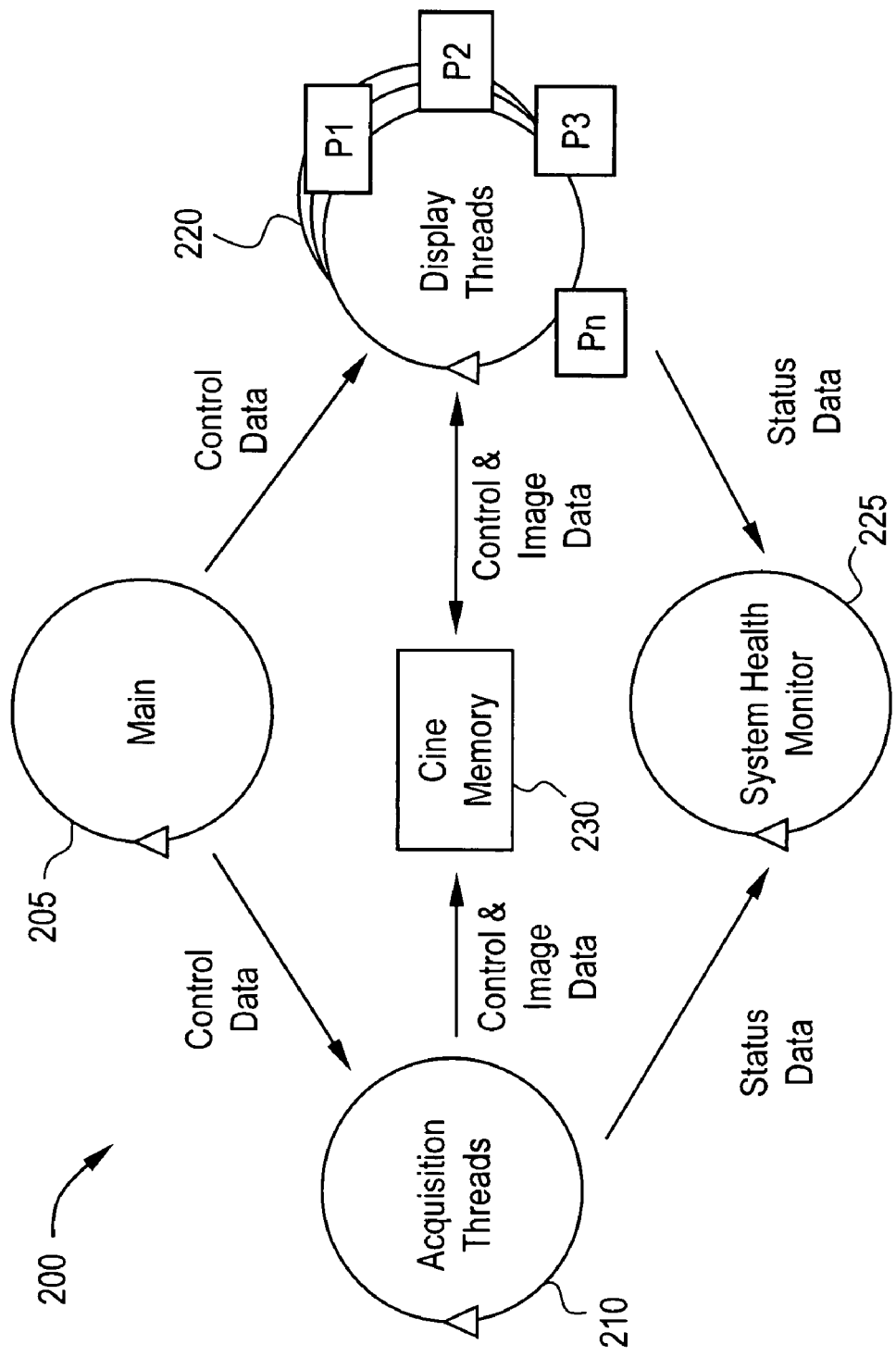
FIG. 2 illustrates a data and processing flow model for a medical imaging system according to an embodiment of the present invention.

FIG. 2 illustrates a data and processing flow model 200 for a medical imaging system according to an embodiment of the present invention. The model 200 includes a main thread 205, one or more acquisition threads 210, one or more display threads 220, a system health monitor 225, and a memory 230. Although some components in the model 200 are illustrated as threads, it should be understood that other execution contexts may be used, such as one or more processes or tasks, for example. That is, components in the model 200 may be implemented as, for example, one or more processes, one or more threads within one or more processes, and/or one or more routines within one or more execution contexts.

The acquisition thread(s) 210 may run on and/or control an acquisition subsystem, for example. The acquisition subsystem may be similar to the acquisition subsystem 110, described above, for example. The acquisition thread(s) 210 may run on and/or control acquisition hardware, for example. The acquisition hardware may be similar to the acquisition hardware 115, described above, for example.

The display thread(s) 220 may run on and/or control a processing component, for example. The processing component may be similar to and/or include the image display subsystem 120, described above, for example. The display thread(s) 220 may include display and/or processing routines. The display routines may be configured to display signal and/or image data, for example. The processing routines may be configured to process signal and/or image data, for example. For example, each display thread 220 may be associated with a processing module similar to the processing modules described above.

The signal and/or image data may be stored in the memory 230, for example. The memory 230 may be similar to the memory component 130, described above, for example.

The main thread 205 is in communication with one or more of the acquisition threads 210 and one or more of the display threads 220. The main thread 205 may communicate control data to the acquisition thread(s) 210 and/or the display thread(s) 220, for example. The acquisition thread(s) 210 and the display thread(s) 220 are in communication with the memory 230 and the system health monitor 225. The acquisition thread(s) 210 and/or the display thread(s) 220 may communicate control and/or image data to the memory 230. The acquisition thread(s) 210 and/or the display thread(s) 220 may communicate status data to the system health monitor 225.

In operation, the main thread 205 controls the acquisition thread(s) 210 and the display thread(s) 220. The main thread 205 may communicate control data to the acquisition thread(s) 210 and/or the display thread(s) 220, for example. For example, the main thread 205 may communicate control data to an acquisition thread 210 indicating that signal data is to be acquired. As another example, the main thread 205 may communicate control data to both the acquisition thread(s) 210 and the display thread(s) 220 indicating that a diagnostic test should be initiated and the results should be passed to the system health monitor 225 and displayed to a user.

The acquisition thread(s) 210 may acquire signal data and store it in the memory 230. The acquisition thread(s) 210 may acquire the signal data based on a command from the main thread 205, for example. The acquisition thread(s) 210 may acquire the signal data using the acquisition hardware 115, for example. As another example, the acquisition thread(s) 210 may acquire diagnostic signal data by providing one or more diagnostic vectors to the acquisition hardware 115.

In certain embodiments, the acquisition thread(s) 205 may communicate some or all of the acquired data to the system health monitor 225. For example, an acquisition thread 205 may communicate parameters of one or more vectors in the scan sequence used to generate signal data. As another example, the acquisition threads 205 may provide frames of signal data and associated tags indicating what type of data is in the frames.

The display thread(s) 220 may process and/or display signal and/or image data. The signal and/or image data may be stored in the memory 230, for example. The display thread(s) 220 may process the signal data to generate the image data. For example, a first display thread 220 may process a frame of signal data stored in the memory 230 to generate an image, then a second display thread 220 may process the generated image further to enhance it. Finally, a third display thread 220 may display the enhanced image to a user.

The display thread(s) 220 may include and/or may be included in one or more processing modules. For example, each processing module may run in its own thread. As another example, a thread may drive more than one processing module. A processing module may be adapted to process and/or transform signal and/or image data. For example, a processing module may transform a frame of B-mode signal data into a B-mode image. As another example, a processing module may communicate a color Doppler image to a user interface such as interface component 140 for display to a user.

In certain embodiments, one or more display thread(s) 220 may process the diagnostic signal data. For example, the diagnostic signal data may be acquired by one or more acquisition thread(s) 210 based at least in part on diagnostic vectors. The diagnostic signal data may be stored in the memory 230, for example. The diagnostic signal data may be processed to determine a diagnostic status of one or more components of an imaging system such as medical imaging system 100, for example. The display thread(s) 220 may display the diagnostic signal data and/or the diagnostic status to a user, for example. As another example, the display thread(s) 220 may communicate the processed diagnostic signal data to the system health monitor 225 for further processing and/or analysis.

The system health monitor 225 may receive data from the acquisition thread(s) 210 and/or the display thread(s) 220. In certain embodiments, the system health monitor 225 receives data from the memory 230. The system health monitor 225 may run on the processing component of the display thread(s) 220, for example.

The data may include status data and/or signal data, such as a diagnostic status and/or diagnostic signal data. For example, the acquisition thread(s) 210 may provide status data regarding the configuration of a diagnostic vector that was used to acquire diagnostic signal data. As another example, a display thread 220 may provide processed diagnostic signal data to the system health monitor 225 for further processing and/or analysis.

The system health monitor 225 is adapted to monitor data to detect faults in an image system. The system health monitor 225 may trigger and/or initiate diagnostic tests. The diagnostic tests may be initiated periodically. As discussed above, one or more diagnostic vectors may be inserted into the scan sequence at a variety of points in time and/or under a variety of conditions. For example, one or more diagnostic vectors may be fired just prior to the suspension of scanning when the imaging system is entering freeze mode. As another example, a diagnostic vector may be inserted into the scan sequence once per frame. As another example, a diagnostic vector may be triggered in place of a conditioning vector.

In certain embodiments, the system health monitor 225 is adapted to analyze, process, log, and/or notify a user regarding diagnostic signal data and/or a diagnostic status received from the acquisition thread(s) 210 and/or the display thread(s) 220. For example, the system health monitor 225 may, during normal system operation, periodically initiate diagnostic tests of various subcomponents of a medical imaging system such as medical imaging system 100, analyze the acquired diagnostic signal data, and log the results of the analysis. In addition, the system health monitor 225 may alert a field service engineer to anomalies detected in the status of components of the imaging system so that repairs may be performed before components fail. Similarly, in certain embodiments, the system health monitor 225 is adapted to log and/or notify a user based on its analysis of the received diagnostic status.

As discussed above, the components, elements, and/or functionality of the medical imaging system illustrated in the model 200 may be implemented alone or in combination in various forms in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Figure 3:
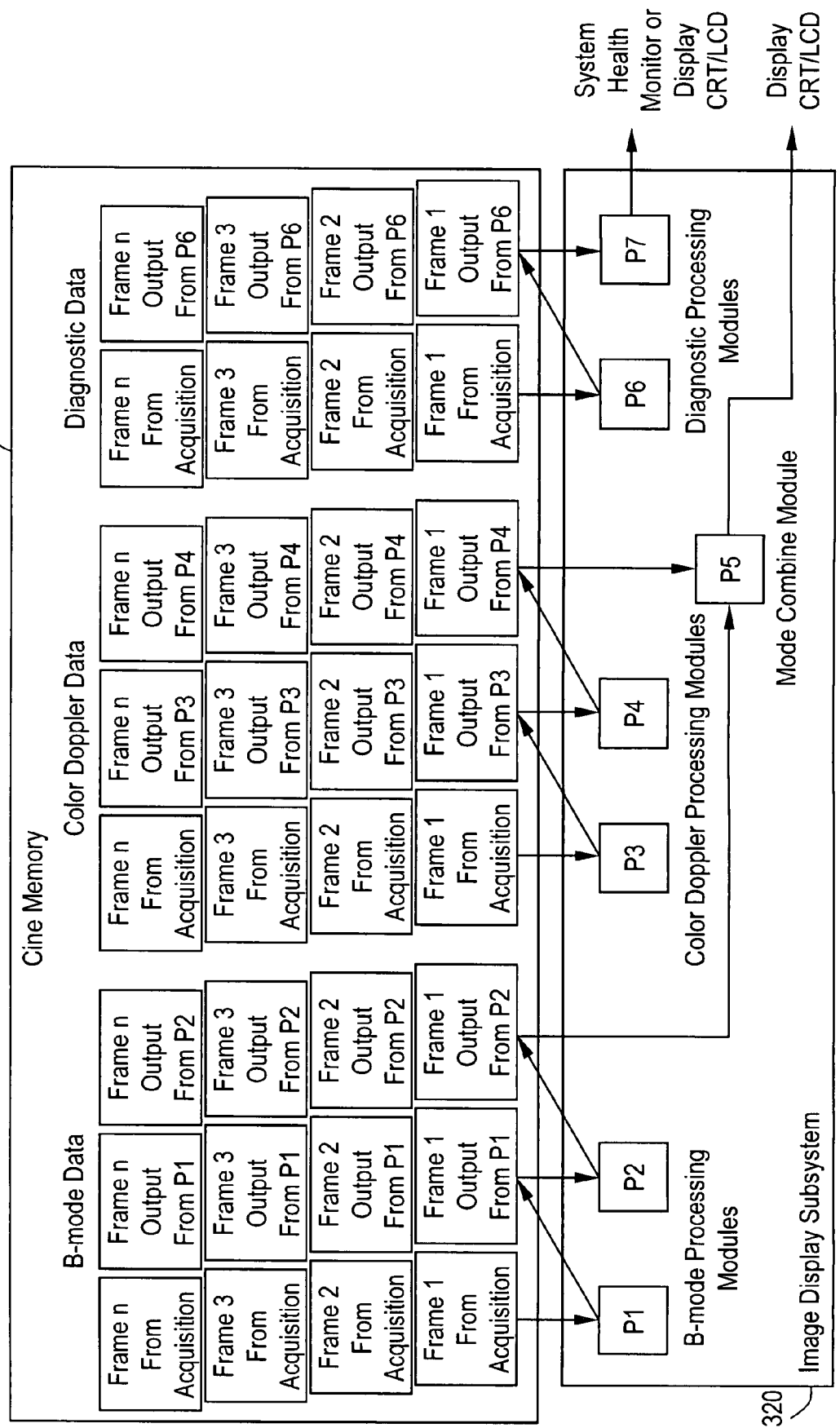
FIG. 3 illustrates the processing flow in a image processing and display subsystem of a medical imaging system according to an embodiment of the present invention.

FIG. 3 illustrates the processing flow in a image processing and display subsystem 300 of a medical imaging system according to an embodiment of the present invention. The subsystem 300 includes an image display subsystem 320 and a memory component 330. The subsystem 300 may be referred to as the back-end of the medical imaging system.

The image display subsystem 320 may be similar to the image display subsystem 120, described above, for example. The memory component 330 may be similar to the memory component 130, described above, for example. The image display subsystem 320 is in communication with the memory component 330.

In operation, the memory component 330 may include one or more acquired frames. The frames may have been acquired from acquisition hardware similar to the acquisition hardware 115, described above, for example. The frames may include data for one or more modes of operations and/or types of vectors. For example, as illustrated in FIG. 3, the memory component 330 includes frames include B-mode data, color Doppler data, and diagnostic data.

The one or more frames in the memory component 330 may be processed by one or more processing modules in the image display subsystem 320. The processing modules may be similar to the processing modules described above with reference to FIG. 2, for example. As discussed above, processing modules may be chained together. For example, as illustrated in FIG. 3, the processing for B-mode data in the memory component 330 may involve processing by processing modules P1 and P2. P1 may, for example, process frames of acquired signal data and store the result of its processing back in the memory component 330. The acquired signal data may be acquired by acquisition hardware such as acquisition hardware 115, described above, for example. The frames output as a result of the processing by processing component P1 may in turn by processed by module P2. Similarly, color Doppler data may be processed by P3 and P4. The processed B-mode and color Doppler data may then be processed by processing module P5, which may, for example, combine the data to form a composite image. P5 may also provide the resulting processed data to a display. The display may be part of an interface component such as interface component 140, described above, for example.

In certain embodiments, the subsystem 300 includes one or more processing modules for processing diagnostic data. The processing modules may be similar to the processing modules discussed above, for example. Similarly, the processing modules for handling diagnostic data may be chained together. For example, as illustrated in FIG. 3, the processing module P6 may retrieve diagnostic signal data from the memory component 330. After processing the diagnostic signal data, the processing module P6 may store the processed diagnostic signal data back in the memory component 330 so that processing module P7 may in turn further process it. Alternatively, the processing module P6 may pass the processed diagnostic signal data directly to processing module P7.

After processing of the diagnostic signal data is complete, it may be displayed. For example, the processed diagnostic signal data may be communicated to an interface, such as interface component 140, to be displayed to a user. As another example, the processed diagnostic signal data may be communicated to a system health monitor similar to the system health monitor 225, described above.

Returning to the example of the channel-alive test discussed above, once the signal data based on the fired diagnostic vectors has been received by the acquisition hardware 115, it may be read out and stored in memory similar to the memory component 330. One or much diagnostic processing modules, such as modules P6 and P7 may analyze the frames of the diagnostic signal data to determine whether each system channel contained valid information. The analysis may determine a diagnostic status for each channel, for example. After processing is completed, the resulting data and/or status may be communicated to a system health monitor such as system health monitor 225, described above, for example. The resulting data and/or status may include, for example, the operating condition of each channel. The system health monitor may then log the data for future reference by on-site or remote service personnel or send an alert to a field service engineer indicating a potential fault has been detected. Alternatively, the resulting data and/or status may be displayed to a user such as a field service representative when a service key is in place in the imaging system.

As discussed above, the components, elements, and/or functionality of the image processing and display subsystem 300 may be implemented alone or in combination in various forms in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Figure 4:
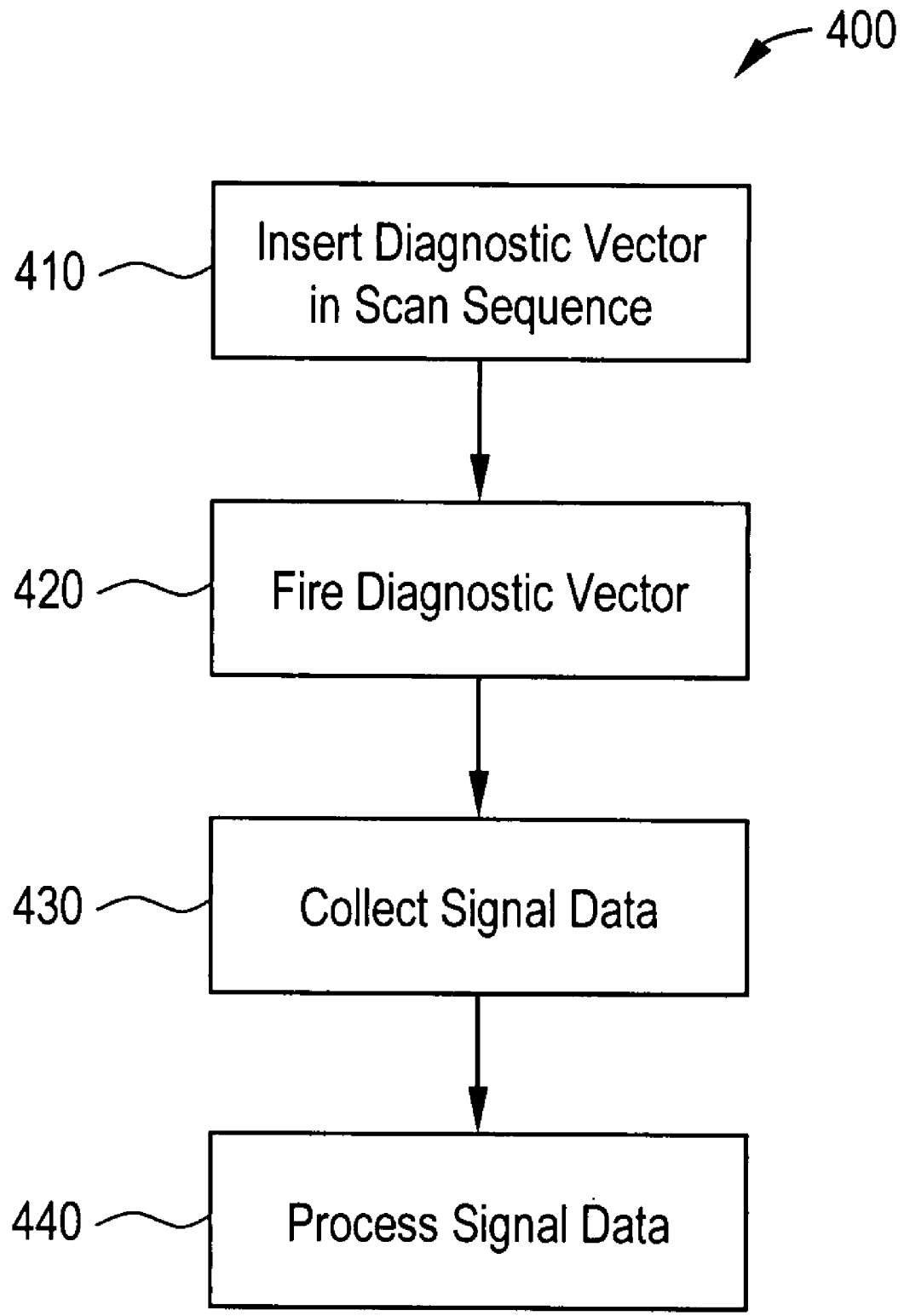
FIG. 4 illustrates a flow diagram for a method for performing diagnostics in a medical imaging system during the normal operating mode of the imaging system in accordance with an embodiment of the present invention.

FIG. 4 illustrates a flow diagram for a method 400 for performing diagnostics in a medical imaging system during the normal operating mode of the imaging system in accordance with an embodiment of the present invention. The method 400 includes the following steps, which will be described below in more detail. At step 410, a diagnostic vector is inserted in to a scan sequence. At step 420, a diagnostic vector is fired. At step 430, signal data is collected. At step 440, signal data is processed. The method 400 is described with reference to elements of systems described above, but it should be understood that other implementations are possible.

At step 410, a diagnostic vector is inserted in to a scan sequence. The diagnostic vector may be similar to the diagnostic vectors discussed above, for example. The diagnostic vector may be adapted to acquire data relating to one or more components of a medical imaging system. That is, the design and setup of each diagnostic vector may be customized for the part of the system to be tested. The medical imaging system may be similar to the medical imaging system 100, described above, for example.

In certain embodiments, one or more diagnostic vectors may be inserted into the scan sequence at a number of times. In certain embodiments, one or more diagnostic vectors are inserted into the scan sequence during normal operation of the medical imaging system. Multiple diagnostic vectors may be inserted into the scan sequence consecutively, for example. Alternatively, multiple diagnostic vectors may be inserted in the scan sequence separated by one or more non-diagnostic vectors, such as B-mode or color Doppler vectors.

In certain embodiments, the diagnostic vector may be inserted into the scan sequence once per frame. In certain embodiments, a diagnostic vector is inserted into the scan sequence when the imaging system is idle. In certain embodiments, a diagnostic vector is inserted into a scan sequence in place of a conditioning or junk vector. For example, rather than inserting a conditioning vector for which signal data may be ignored, the diagnostic vector may be inserted which can serve a similar purpose as the conditioning vector and may be used to acquire diagnostic status information relating to one or more components of the medical imaging system 100.

In certain embodiments, the diagnostic vector may inserted into the scan sequence to be fired when the probe is in the air. For example, in the case of an ultrasound probe, when the probe is not in contact with the object being imaged, the medical imaging system 100 may be capable of determining this and may take the opportunity to insert the diagnostic vector into the scan sequence.

In certain embodiments, the diagnostic vector may be inserted into the scan sequence when the medical imaging system is about to enter a freeze mode. That is, just prior to entering the freeze mode, one or more diagnostic vectors may inserted into the scan sequence to be fired. For example, a user may indicate via the interface component 140 that the medical imaging system 100 is to be placed into a freeze mode. Before engaging the freeze mode, the medical imaging system 100 may insert the diagnostic vector into the scan sequence to take the opportunity to perform one or more diagnostic tests when the diagnostic vector and/or the diagnostic tests will not interfere with normal imaging operations.

Similarly, in certain embodiments, the diagnostic vector may be inserted into the scan sequence when the medical imaging system is about to come out of freeze to resume scanning. That is, just prior to leaving the freeze mode, one or more diagnostic vectors may be inserted into the scan sequence to be fired. For example, a user may indicate via the interface component 140 that the medical imaging system 100 is to be taken out of freeze mode. Before resuming scanning, the medical imaging system 100 may insert one or more diagnostic vectors into the scan sequence to take the opportunity to perform one or more diagnostic tests when they will not interfere with normal imaging operations.

At step 420, a diagnostic vector is fired. The diagnostic vector may be fired based on a scan sequence, for example. The diagnostic vector may be the diagnostic vector inserted in the scan sequence at step 410, described above, for example. The diagnostic vector may be fired by acquisition hardware such as acquisition hardware 115, described above, for example.

As discussed above, the diagnostic vector may be fired under a variety of conditions. For example, the diagnostic vector may be fired after a predetermined period of time. As another example, the diagnostic vector may be fired just prior to the medical imaging system entering freeze mode.

At step 430, signal data is collected. The signal data may be collected based on a diagnostic vector. For example, the signal data may be reflected energy from the diagnostic vector fired at step 420, described above, for example.

The signal data may be read out of the acquisition hardware and stored in memory. The memory may be similar to the memory component 130, the memory 230, and/or the memory component 330, discussed above, for example. The signal data from one or more diagnostic vectors may be stored in a frame, for example.

At step 440, signal data is processed. The signal data may be the signal data collected at step 430, for example. The signal data may include diagnostic signal data, for example. The signal data may be processed by an image display subsystem similar to image display subsystem 120, described above, for example. The signal data may be processed by one or more processing modules such as those described above, for example.

The diagnostic signal data may be processed to determine a diagnostic status of one or more components of a medical imaging system, such as medical imaging system 100, for example. The diagnostic status may then be displayed to a user, reported to a field service engineer, provided to a system health monitoring component for analysis, and/or stored in a log file, for example.

One or more of the steps of the method 400 may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

Thus, certain embodiments of the present invention provide an active system-health monitoring capability that runs when the system is being used for normal operations. In addition, certain embodiments provide the ability to actively monitor the status of the image chain. Further, certain embodiments of the present invention provide systems and methods for proactive detection of imaging chain problems during normal system operation. Certain embodiments provide the technical effect of an active system-health monitoring capability that runs when the system is being used for normal operations. In addition, certain embodiments provide the technical effect of actively monitoring the status of the image chain. Further, certain embodiments provide the technical effect of proactive detection of imaging chain problems during normal system operation.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for performing diagnostics in a medical imaging system during the normal operating mode of the imaging system, the method including:
    inserting a diagnostic vector in a scan sequence to fire when a probe is in air;
    firing the diagnostic vector with the probe;
    collecting signal data based at least in part on the diagnostic vector; and
    processing the signal data to determine a diagnostic status, wherein the diagnostic status indicates an operating condition of at least one component of the medical imaging system.

2. The method of claim 1, wherein the firing step includes firing a plurality of diagnostic vectors.

3. The method of claim 1, wherein the diagnostic vector is configured to aid in determining the operating condition of the at least one component of the imaging system.

4. The method of claim 1, wherein the diagnostic vector is part of a sequence of vectors.

5. The method of claim 1, wherein the collecting step includes collecting a frame of signal data.

6. The method of claim 1, wherein the signal data includes a reflected portion of the diagnostic vector.

7. The method of claim 1, wherein the processing step occurs at a backend processing component of the medical imaging system.

8. The method of claim 1, wherein the diagnostic status indicates an operating condition of a component of the imaging chain of the medical imaging system.

9. The method of claim 1, wherein the diagnostic status indicates an operating condition of a read element of the probe.

10. The method of claim 1, wherein the diagnostic status indicates an operating condition of a read channel of the medical imaging system.

11. The method of claim 1, wherein the diagnostic vector is inserted in the scan sequence to fire when a predetermined time interval has elapsed.

12. The method of claim 1, wherein the diagnostic vector is inserted in the scan sequence to fire about immediately before normal imaging operation is suspended.

13. The method of claim 1, wherein the diagnostic vector is inserted in the scan sequence to fire about immediately before normal imaging operation is initiated.

14. A system for evaluating the status of a medical imaging system, the system including:
- an acquisition component, wherein the acquisition component is adapted to insert a diagnostic vector in a scan sequence to fire when a probe is in air, wherein the acquisition component is adapted to fire the diagnostic vector during normal system operation, wherein the acquisition component is adapted to collect a signal based at least in part on the diagnostic vector; and
- a processing component, wherein the processing component is adapted to determine a diagnostic status of a component of the medical imaging system based at least in part on the signal.

15. The system of claim 14, further including a system health monitor, wherein the system health monitor is adapted to analyze the diagnostic status.

16. The system of claim 15, wherein the system health monitor is adapted to notify a user based on the analysis of the diagnostic status.

17. The system of claim 14, wherein the processing component includes one or more processing modules for determining the diagnostic status.

18. A computer-readable medium including a set of instructions for execution on a computer, the set of instructions including:
- an insertion routine, wherein the insertion routine is configure to insert a diagnostic vector in a scan sequence to fire when a probe is in air;
- a firing routine, wherein the firing routine is configured to fire the diagnostic vector;
- an acquisition routine, wherein the acquisition routine is configured to collect a signal based at least in part on the diagnostic vector; and
- a processing routine, wherein the processing routine is configured to determine a diagnostic status of a component of a medical imaging system based at least in part on the signal.

* * * * *

UNITED STATES PATENT AND TRADEMARK OFFICE
CERTIFICATE OF CORRECTION

| | | |
|---|---|---|
| PATENT NO. | : 7,415,371 B2 | Page 1 of 1 |
| APPLICATION NO. | : 11/490289 | |
| DATED | : August 19, 2008 | |
| INVENTOR(S) | : Sabourin et al. | |

It is certified that error appears in the above-identified patent and that said Letters Patent is hereby corrected as shown below:

Title page, item (75) Inventors:   delete "Mortiz" and insert --Moritz--.

Signed and Sealed this

Twentieth Day of January, 2009

JON W. DUDAS
*Director of the United States Patent and Trademark Office*